US012674877B2

(12) United States Patent
Oguz et al.

(10) Patent No.: US 12,674,877 B2
(45) Date of Patent: Jul. 7, 2026

(54) DEVICE FOR ANALYSING A PASSENGER COMPARTMENT OF A VEHICLE

(71) Applicant: VALEO COMFORT AND DRIVING ASSISTANCE, Créteil (FR)

(72) Inventors: Onur Oguz, Créteil (FR); Pierre Avital, Créteil (FR); Georges Djokic, Créteil (FR)

(73) Assignee: VALEO COMFORT AND DRIVING ASSISTANCE, Créteil (FR)

( * ) Notice: Subject to any disclaimer, the term of this patent is extended or adjusted under 35 U.S.C. 154(b) by 357 days.

(21) Appl. No.: 18/018,372

(22) PCT Filed: Jun. 14, 2021

(86) PCT No.: PCT/EP2021/065965
§ 371 (c)(1),
(2) Date: Jan. 27, 2023

(87) PCT Pub. No.: WO2022/022883
PCT Pub. Date: Feb. 3, 2022

(65) Prior Publication Data
US 2023/0305130 A1 Sep. 28, 2023

(30) Foreign Application Priority Data
Jul. 28, 2020 (FR) ...................................... 2007948

(51) Int. Cl.
*G01S 13/04* (2006.01)
*A61B 5/0205* (2006.01)
(Continued)

(52) U.S. Cl.
CPC ............ *G01S 13/04* (2013.01); *A61B 5/0205* (2013.01); *B60R 21/01512* (2014.10); *G01S 13/0209* (2013.01)

(58) Field of Classification Search
CPC ...... G01S 13/04; G01S 13/0209; G01S 13/56; B60R 21/01512; B60R 21/01534; A61B 5/0205; B60W 40/08
See application file for complete search history.

(56) References Cited

U.S. PATENT DOCUMENTS 6,474,683 B1 11/2002 Breed et al.
11,127,119 B1 * 9/2021 Slutsky ..................... G06T 5/60
(Continued)

FOREIGN PATENT DOCUMENTS

DE 102005020847 A1 11/2006
KR 20170055352 A * 5/2017 ............. A61B 5/747
(Continued)

OTHER PUBLICATIONS

KR20170055352AtranslationOnly.pdf, machine translation of KR-20170055352-A (Year: 2017).*
(Continued)

*Primary Examiner* — William Kelleher
*Assistant Examiner* — Kenneth W Good
(74) *Attorney, Agent, or Firm* — Osha Bergman Watanabe & Burton LLP

(57) ABSTRACT

An analysis device for analyzing a passenger compartment of a vehicle to detect persons is disclosed. The device has at least one ultra-wideband transceiver configured to transmit a signal (S1) on a wireless communication channel, at least one ultra-wideband transceiver configured to receive a signal (S2) corresponding to the transmitted signal (S1), to compute at least one impulse response (CIR) of the wireless communication channel from said received signal (S2), and to transmit said at least one impulse response (CIR) of the wireless communication channel to an electronic control unit. The electronic control unit is configured to determine biometric features (B) and/or volumetric occupancy features
(Continued)

Figure 1:
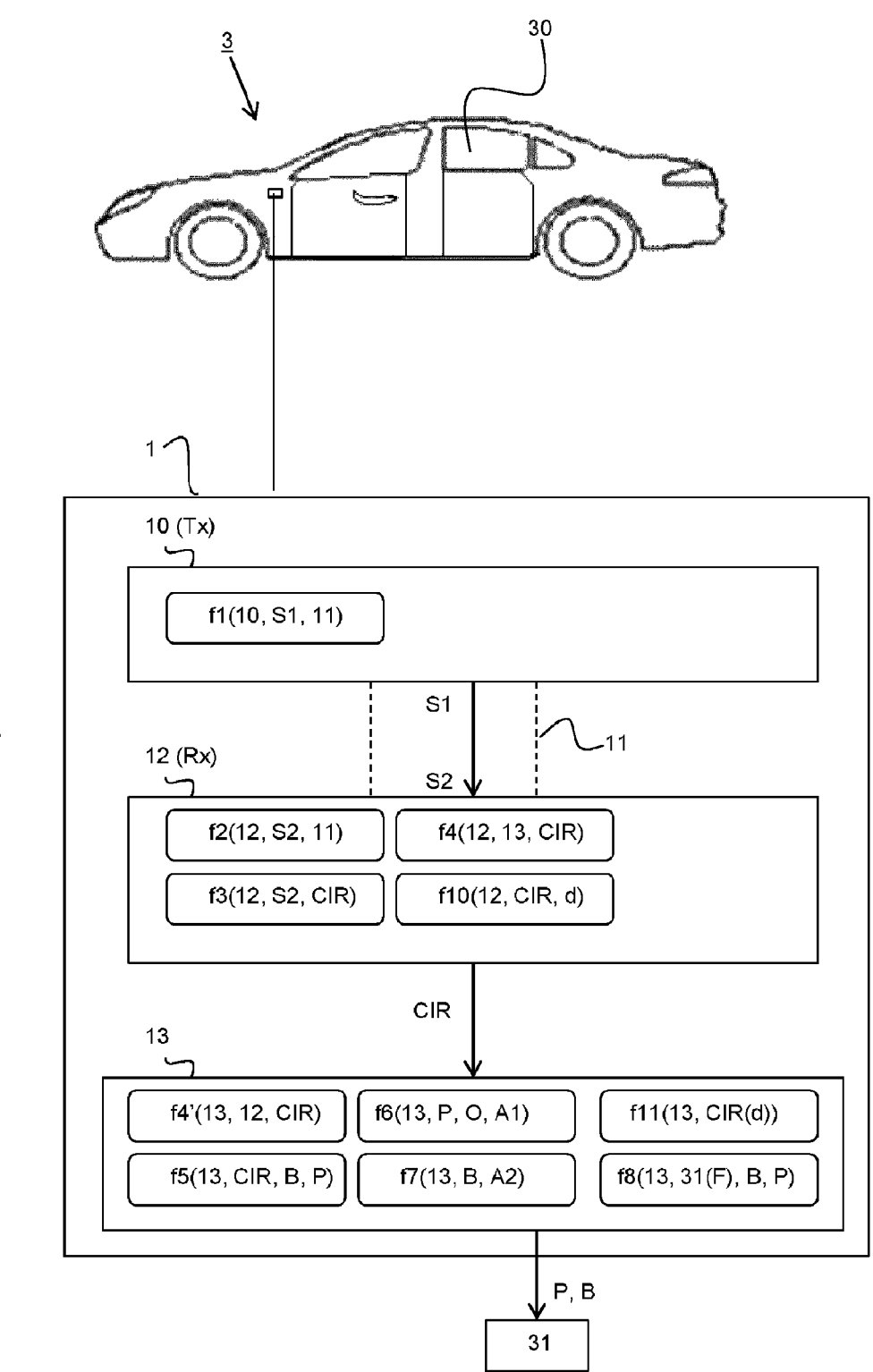

(P) of the passenger compartment on the basis of said at least one impulse response (CIR) of the wireless communication channel.

15 Claims, 8 Drawing Sheets

(51) Int. Cl.
  B60R 21/015        (2006.01)
  G01S 13/02         (2006.01)

(56)                References Cited

U.S. PATENT DOCUMENTS

| | | | |
|---|---|---|---|
| 2006/0208169 A1 | 9/2006 | Breed et al. | |
| 2020/0250447 A1* | 8/2020 | Kaur | A61B 5/117 |
| 2020/0348406 A1* | 11/2020 | Jain | G01S 13/0209 |
| 2021/0241428 A1* | 8/2021 | Mansour | G06T 5/73 |
| 2022/0020488 A1* | 1/2022 | Kennedy | G16H 20/40 |
| 2022/0308195 A1* | 9/2022 | Zeng | G01S 13/003 |

FOREIGN PATENT DOCUMENTS

| | | | | |
|---|---|---|---|---|
| KR | 20200047807 A | 5/2020 | | |
| WO | 02/42124 A2 | 5/2002 | | |
| WO | WO-2019125097 A1 * | 6/2019 | | A61B 3/11 |

OTHER PUBLICATIONS

18018372_2025-03-04_WO_2019125097_A1_M.pdf, machine translation of WO-2019125097-A1 (Year: 2019).*

International Search Report and Written Opinion in corresponding International Application No. PCT/EP2021/065965, mailed Aug. 26, 2021 (13 pages).

* cited by examiner

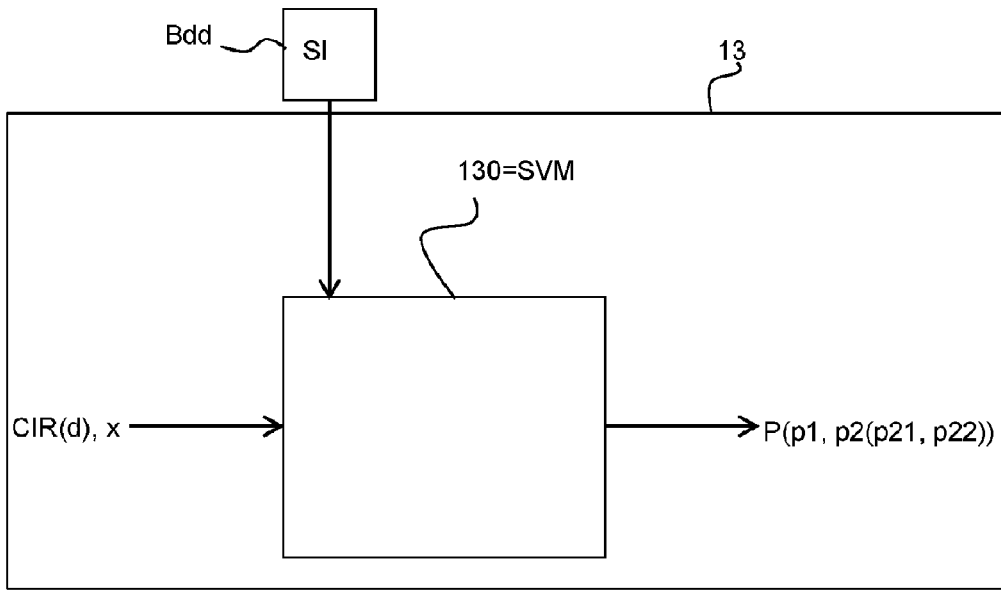
Fig.9
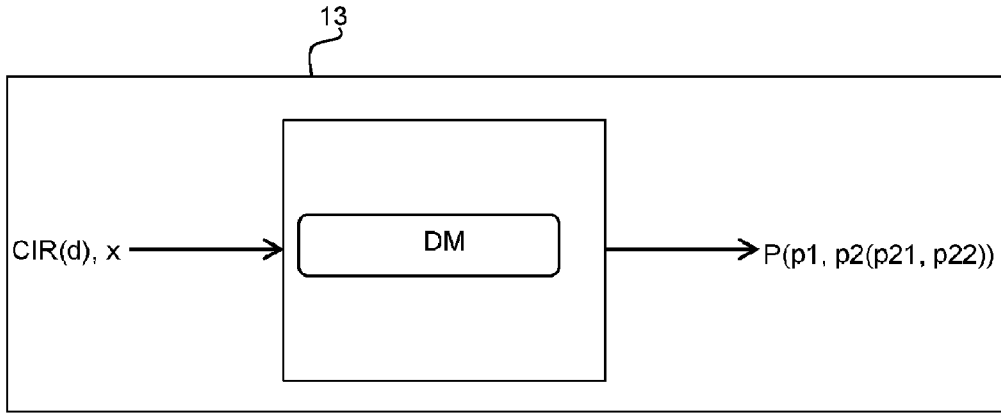
Fig.10
Fig. 11

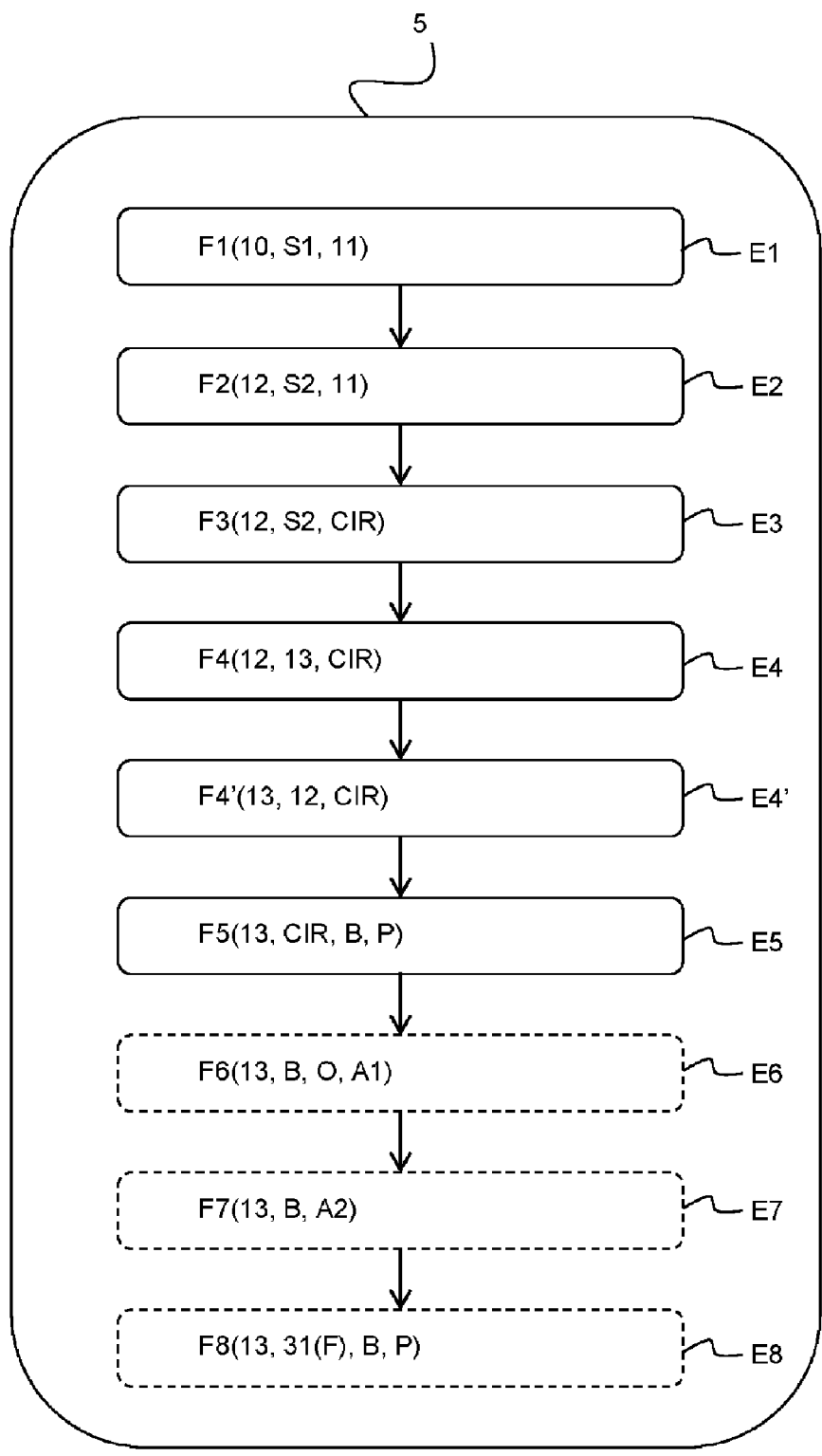
<u>Fig. 12</u>

DEVICE FOR ANALYSING A PASSENGER COMPARTMENT OF A VEHICLE

The present invention relates to an analysis device for analyzing a vehicle passenger compartment. It is particularly but nonlimitingly applicable to motor vehicles.

In the field of motor vehicles, an analysis device for analyzing a vehicle passenger compartment comprises a dedicated system of 89-GHz sensors for analyzing the passenger compartment. This analysis may be used for example in order to detect the presence of at least one person in the passenger compartment of the vehicle or the absence of persons in the passenger compartment.

A disadvantage of this prior art is that this dedicated sensor system is expensive and that if a vehicle is not equipped, it is necessary to equip it with a dedicated sensor system of this kind in order to be able to carry out presence detection.

In this context, the present invention aims to propose an analysis device for analyzing a passenger compartment of a vehicle that makes it possible to solve the drawback mentioned above.

To this end, the invention proposes an analysis device for analyzing a passenger compartment of a vehicle in order to detect persons, characterized in that said analysis device comprises:

- at least one ultra-wideband transceiver configured to transmit a signal on a wireless communication channel,
- at least one ultra-wideband transceiver configured to receive a signal corresponding to the transmitted signal, to compute at least one impulse response of the wireless communication channel from said received signal, and to transmit said at least one impulse response of the wireless communication channel to an electronic control unit,
- said electronic control unit configured to determine biometric features and/or volumetric occupancy features of the passenger compartment on the basis of said at least one impulse response of the wireless communication channel.

Thus, as will be seen below, the ultra-wideband transceivers already present in the vehicle, which are normally used for an automatic opening/closing function of the vehicle and/or for an automatic starting function of the vehicle, are used to perform a function for which they are not intended, namely a detection function for detecting a person in the passenger compartment of a vehicle. Thus, it is not necessary to have a system of dedicated sensors.

According to nonlimiting embodiments, said analysis device may further comprise one or more additional features taken individually or in any technically possible combination, from among those that follow.

According to one nonlimiting embodiment, the electronic control unit transmits the biometric features and/or said volumetric occupancy features to an information processing unit in order for the latter to perform a function determined according to the biometric features and/or said volumetric occupancy features.

According to one nonlimiting embodiment, said analysis device comprises an ultra-wideband transceiver configured to transmit a signal and at least two transceivers configured to receive said signal corresponding to said transmitted signal.

According to one nonlimiting embodiment, an ultra-wideband transceiver is configured to be in transmission mode or in reception mode.

According to one nonlimiting embodiment, said electronic control unit is moreover configured to determine the presence of at least one person or the absence of persons in the passenger compartment on the basis of said volumetric occupancy features of the passenger compartment.

According to one nonlimiting embodiment, the volumetric occupancy features of the passenger compartment are a distribution in space, and/or an age category.

According to one nonlimiting embodiment, a distribution in space is:

- an unoccupied passenger compartment,
- an occupancy of the front-right space,
- an occupancy of the front-left space,
- an occupancy of the rear-right space,
- an occupancy of the rear-left space.

According to one nonlimiting embodiment, an age category is:

- a baby,
- a child,
- an adult.

According to one nonlimiting embodiment, said electronic control unit comprises a classifier.

According to one nonlimiting embodiment, said classifier is configured to receive at the input a portion of said at least one impulse response of the communication channel, and a time index for the time at which said impulse response of the communication channel was computed.

According to one nonlimiting embodiment, said classifier is a support vector machine.

According to one nonlimiting embodiment, said electronic control unit is configured to perform a modal decomposition.

According to one nonlimiting embodiment, the biometric features are a respiratory rate and/or a heart rate.

According to one nonlimiting embodiment, said electronic control unit is moreover configured to determine a state of health of at least one person in the passenger compartment of said vehicle on the basis of said biometric features.

According to one nonlimiting embodiment, said electronic control unit is configured to determine said biometric features by means of a spectral analysis.

The invention moreover proposes an analysis method for analyzing a passenger compartment of a vehicle in order to detect persons, characterized in that said analysis method comprises:

- at least one ultra-wideband transceiver transmitting a signal on a wireless communication channel,
- at least one ultra-wideband transceiver receiving a signal corresponding to the transmitted signal,
- said at least one ultra-wideband transceiver computing at least one impulse response of the wireless communication channel from said received signal,
- said at least one ultra-wideband transceiver transmitting said at least one impulse response of the wireless communication channel to an electronic control unit,
- said electronic control unit determining biometric features and/or volumetric occupancy features of the passenger compartment on the basis of said at least one impulse response of the wireless communication channel.

Figure 2:
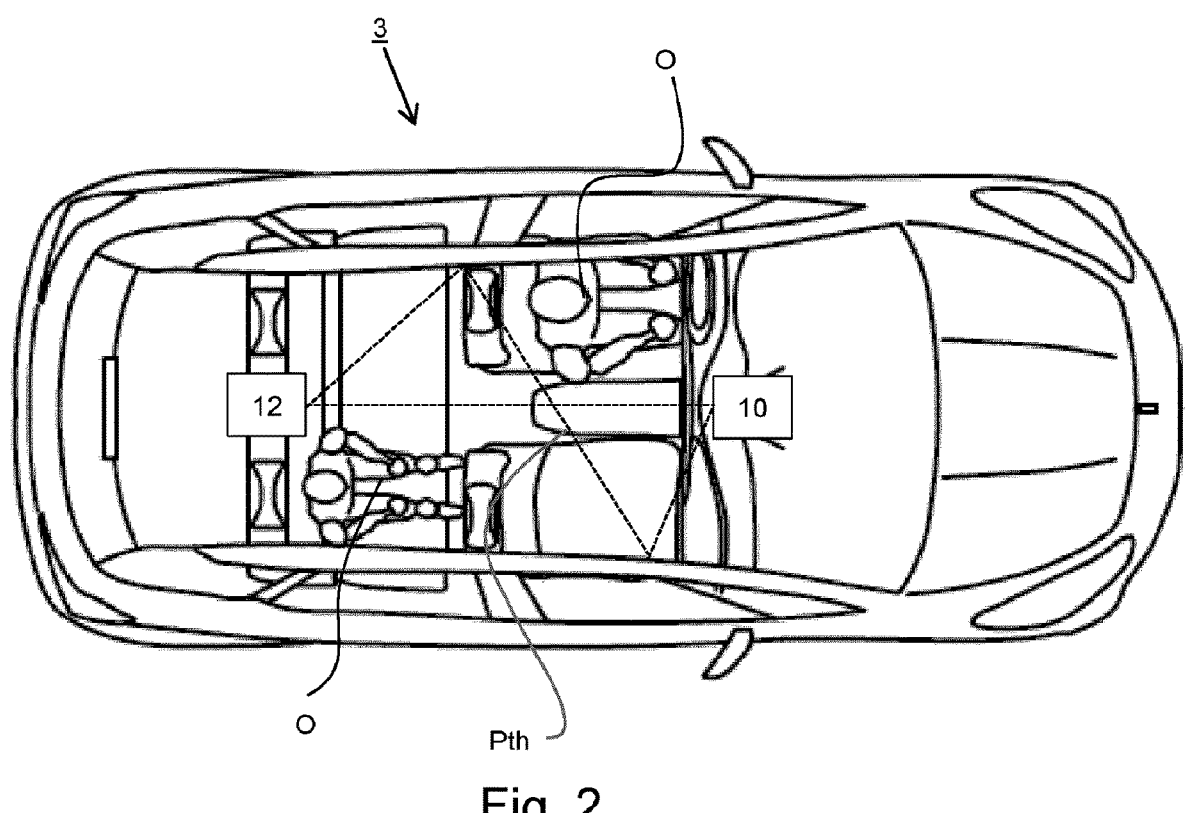
Figure 3:
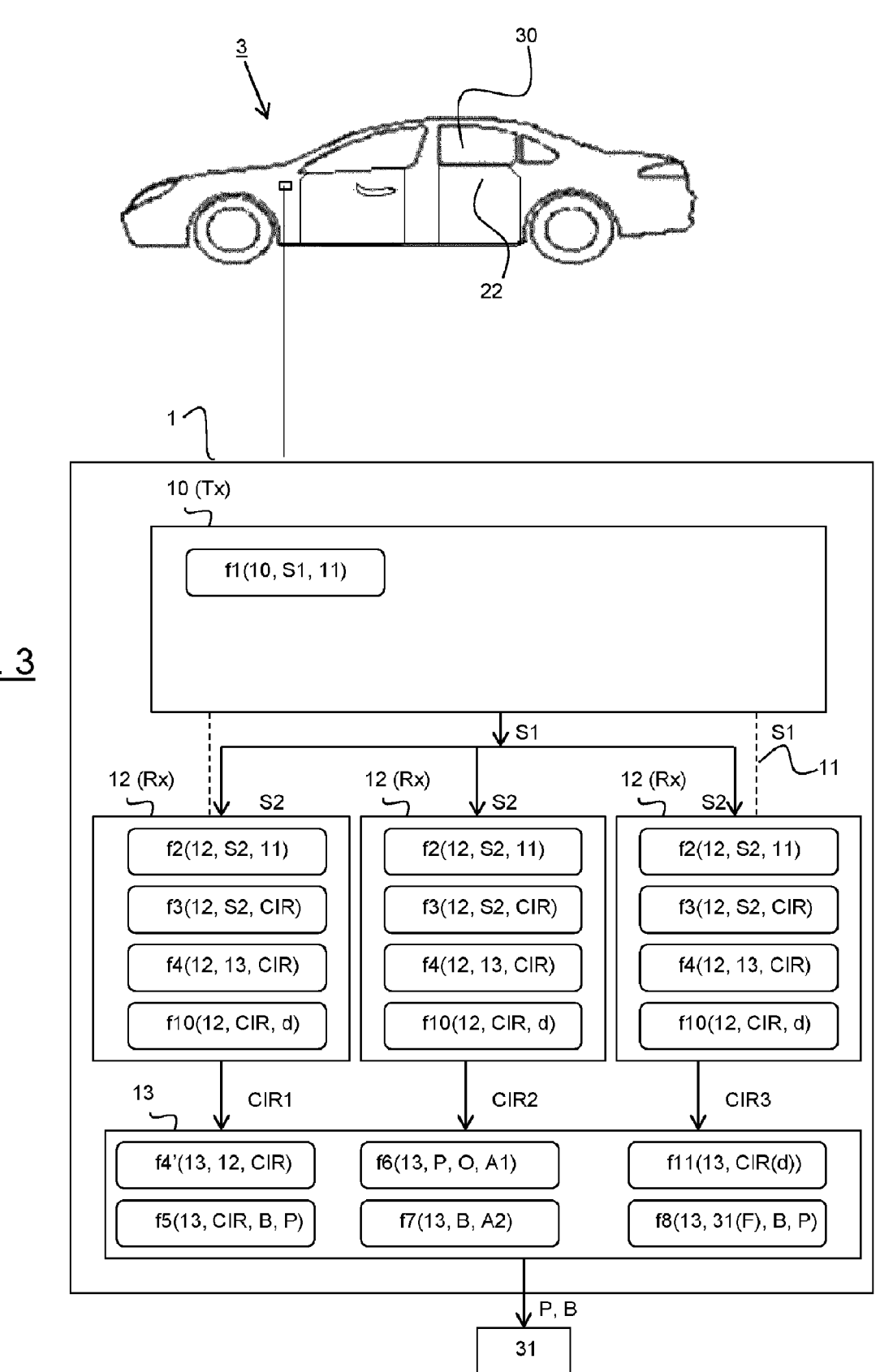
Figure 4:
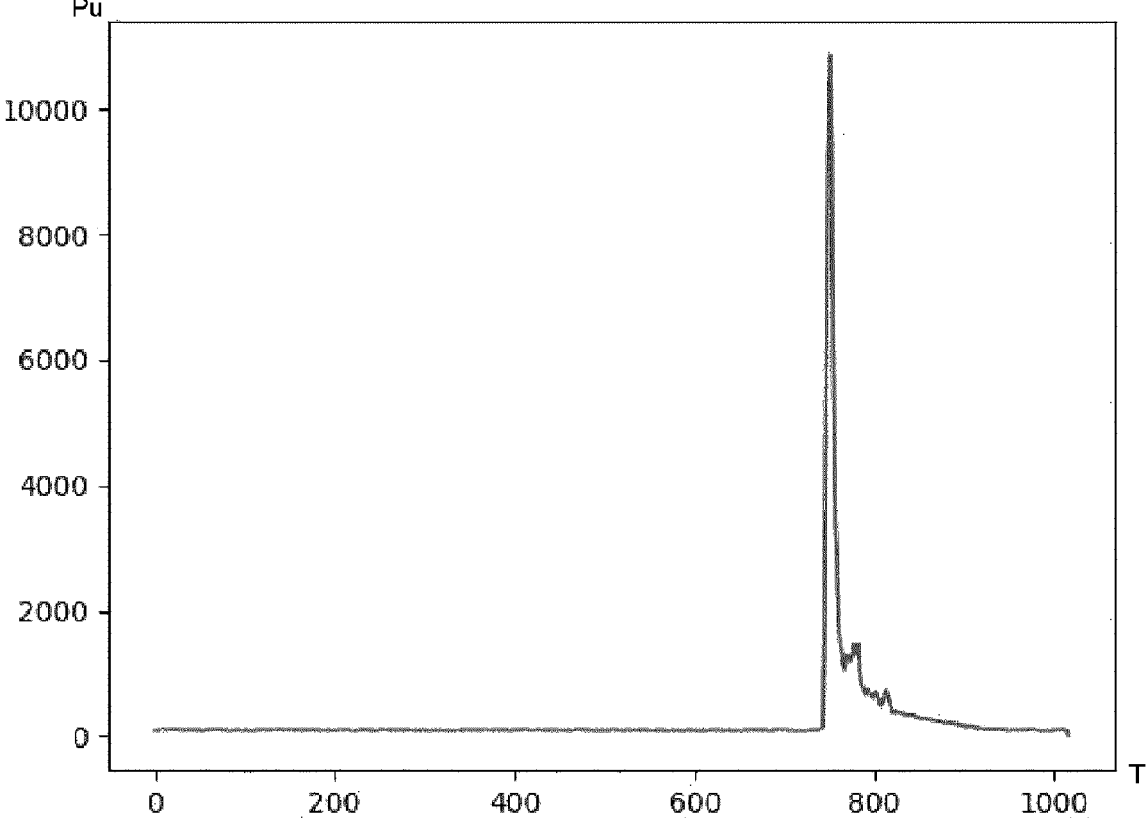
Figures 5, 6:
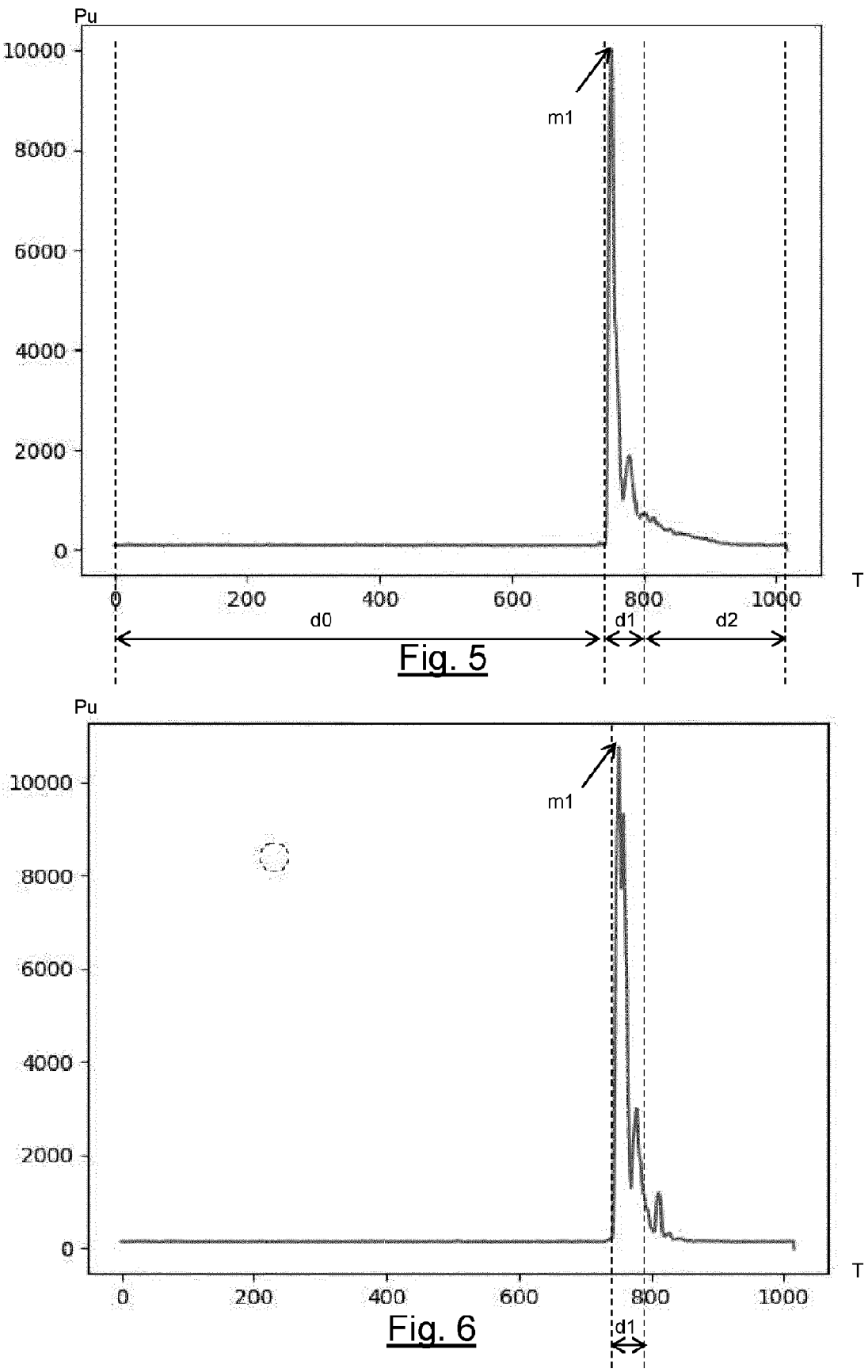
Figures 7, 8:
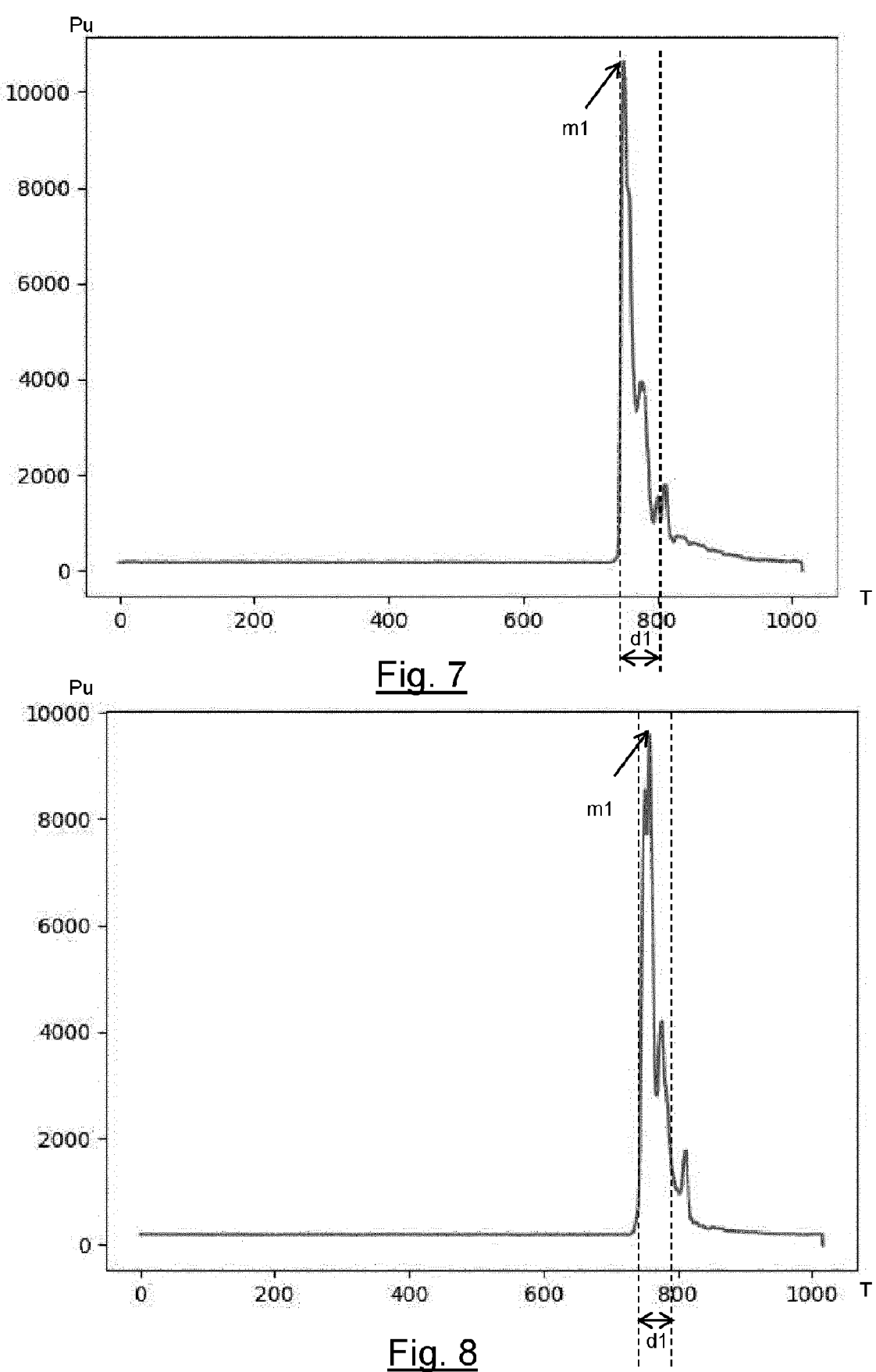

The invention and the various applications thereof will be better understood on reading the following description and on examining the accompanying figures, in which:

FIG. 1 is a schematic view of an analysis device for analyzing a vehicle passenger compartment, said analysis device comprising two transceivers configured to communicate via a wireless communication channel, and an electronic control unit, according to a first nonlimiting embodiment of the invention, FIG. 2 is a top view of a vehicle in which there are two persons, the top view schematically illustrating the two transceivers of the analysis device in FIG. 1 according to one nonlimiting embodiment, FIG. 3 is a schematic view of an analysis device for analyzing a vehicle passenger compartment, said analysis device comprising four transceivers configured to communicate via a wireless communication channel, and an electronic control unit, according to a second nonlimiting embodiment of the invention, FIG. 4 is a first example of an impulse response of the wireless communication channel in FIGS. 1 to 3 when the passenger compartment of the vehicle is unoccupied, according to one nonlimiting embodiment, FIG. 5 is a second example of an impulse response of the wireless communication channel in FIGS. 1 to 3 when the passenger compartment of the vehicle is occupied, according to one nonlimiting embodiment, FIG. 6 is a third example of an impulse response of the wireless communication channel in FIGS. 1 to 3 when the passenger compartment of the vehicle is occupied, according to one nonlimiting embodiment, FIG. 7 is a fourth example of an impulse response of the wireless communication channel in FIGS. 1 to 3 when the passenger compartment of the vehicle is occupied, according to one nonlimiting embodiment, FIG. 8 is a fifth example of an impulse response of the wireless communication channel in FIGS. 1 to 3 when the passenger compartment of the vehicle is occupied, according to one nonlimiting embodiment, FIG. 9 is a diagram of an electronic control unit of the analysis device in FIG. 1 or in FIG. 3, with its inputs and its outputs, according to a first nonlimiting embodiment, FIG. 10 is a diagram of an electronic control unit of the analysis device in FIG. 1 or in FIG. 3, with its inputs and its outputs, according to a second nonlimiting embodiment, FIG. 11 is a diagram of an electronic control unit of the analysis device in FIG. 1 or in FIG. 3, with its inputs and its outputs, according to a third nonlimiting embodiment, FIG. 12 is a flowchart of a method for analyzing a passenger compartment of a vehicle, implemented by the analysis device in FIG. 1 or in FIG. 3, according to one nonlimiting embodiment.

Elements that are identical in terms of structure or function appearing in various figures retain the same references, unless indicated otherwise.

The analysis device 1 for analyzing a passenger compartment 30 of a vehicle 3 according to the invention is described with reference to FIGS. 1 to 10. In one nonlimiting embodiment, the vehicle 3 is a motor vehicle. In one nonlimiting embodiment, the vehicle 3 is nonautonomous, semiautonomous or autonomous. Motor vehicle is intended to mean any type of motorized or electric vehicle. This embodiment is taken as a nonlimiting example in the remainder of the description. In the remainder of the description, the vehicle 3 is thus also called the motor vehicle 3.

As illustrated in FIG. 1 or FIG. 3, in one nonlimiting embodiment, the analysis device 1 comprises:

at least one ultra-wide-frequency-band transceiver 10 configured to transmit a signal S1 (function f1(10, S1, 11)), at least one ultra-wide-frequency-band transceiver 12 configured to receive a signal S2 corresponding to said transmitted signal S1 (function f2(12, S2, 11)), an electronic control unit 13.

FIG. 2 illustrates a motor-vehicle 3 with two persons O, and a transceiver 10 of the analysis device 1, which communicates with a transceiver 12 of the analysis device 1.

An ultra-wide-frequency-band transceiver, referenced 10 or 12 in the figures, is also called a UWB (ultra-wideband) transceiver. It is recalled that the main band provided for the ultra-wide frequency band is between 3.1 GHz and 10.6 GHz. The signal S1, also called the transmitted signal S1, and the signal S2, also called the received signal S2, are ultra-wideband signals. It is recalled that an ultra-wideband signal is a signal whose −10 dB passband exceeds 500 MHz and 20% of its center frequency at any moment. The transmitted signal S1 is transmitted on the wireless communication channel 11 (illustrated in dotted lines in FIGS. 1 and 3). The received signal S2 is received via this wireless communication channel 11. The transmitted signal S1 takes a propagation path Pth illustrated in FIG. 2. It will be noted that these ultra-wide-frequency-band transceivers are conventionally used for automatically detecting a person approaching a motor vehicle in order to perform an automatic opening/closing function of the motor vehicle, and/or an automatic starting function of the motor vehicle. These functions are commonly called "passive entry—passive start" or referred to as PEPS functions. To this end, for these PEPS functions, these ultra-wide-frequency-band transceivers are conventionally coupled to an identification unit (not illustrated) that the user of the motor vehicle carries.

In the remainder of the description, the ultra-wide-frequency-band transceiver 10 is also called the transceiver 10, and the ultra-wide-frequency-band transceiver 12 is also called the transceiver 12.

An ultra-wide-frequency-band transceiver is configured to be in transmission mode Tx or in reception mode Rx.

The transceiver 10 that is in transmission mode Tx sends the signal S1 periodically. In one nonlimiting example, it transmits the signal S1 every second.

The transceiver 12 that is in reception mode Rx is moreover configured to compute at least one impulse response CIR of the wireless communication channel 11 from said received signal S2 (function f3(12, S2, CIR)). In the remainder of the description, an impulse response CIR of the wireless communication channel 11 is also called the impulse response CIR or the CIR response. This is called the "channel impulse response". An impulse response CIR mirrors all reflections of the transmitted signal S1 from all objects in the surroundings of the motor vehicle 3 (persons, trees, other vehicles, buildings, etc.) and from all persons inside the motor vehicle 3. An impulse response CIR is characterized by various amplitudes over various durations. Examples of impulse responses CIR are illustrated in FIGS. 4 to 8, which are explained later on in the description. The abscissa shows the time of flight T of a reflected signal stemming from the transmitted signal S1, and the ordinate shows its power Pu. The time of flight T corresponds to a distance of the object from which the transmitted signal S1 is reflected, in other words to the propagation path Pth taken by the signal S1 to the transceiver 12. Thus, courtesy of the impulse responses CIR, the state of the wireless communication channel 11 is monitored. The changes of this state are used to determine volumetric occupancy features P of the passenger compartment 30 and biometric features B. It will be noted that computing an impulse response CIR is part of the inherent functions of UWB transceivers: the transceiver 12 automatically computes a CIR response as soon as it receives a signal S1. In one nonlimiting embodiment, the transceiver 12 computes an impulse response CIR over a window of approximately 1 microsecond.

The transceiver 12 is moreover configured to transmit the impulse response CIR that it has computed to the electronic control unit 13 (function f4(12, 13, CIR)).

The electronic control unit 13 is configured to receive said impulse response CIR (function f4'(13, 12, CIR)). It receives it from the transceiver 12 on a wired communication channel such as, in one nonlimiting example, a CAN (controller area network) data bus.

The electronic control unit 13 is moreover configured to determine biometric features B and/or volumetric occupancy features P of the passenger compartment 30 on the basis of said at least one impulse response CIR (function f5(13, CIR, B, P)).

In one nonlimiting embodiment, the electronic control unit 13 is moreover configured to determine the presence/absence A1 of at least one person O in the passenger compartment 30, namely the presence of at least one person O or the absence of persons O in the passenger compartment 30, on the basis of said volumetric occupancy features P of the passenger compartment 30 (function f6(13, P, O, A1)).

In one nonlimiting embodiment, the electronic control unit 13 is moreover configured to determine a state of health A2 of said at least one person O on the basis of said biometric features B (function f7(13, B, A2)). It will be noted that there may be detection of the presence/absence A1 of at least one person O and/or detection of the state of health A2 of at least one person O.

In one nonlimiting embodiment, the volumetric occupancy features P of the passenger compartment 30 are a distribution in space p1, and/or an age category p2. Any combination of p1 and p2 may be defined.

In one nonlimiting embodiment, an age category p2 is:
baby, and/or
child, and/or
adult.

In one nonlimiting embodiment, a distribution in space p1 is:
an unoccupied passenger compartment 30, or
an occupancy of the front-right space, and/or
an occupancy of the front-left space, and/or
an occupancy of the rear-right space, and/or
an occupancy of the rear-left space.

In one nonlimiting embodiment, the age category p2 may be classified into weight ranges p21, and/or into height ranges p22. The weight ranges p21 and the height ranges p22 thus allow the age categories p2 (baby, child or adult) to be determined.

In one nonlimiting embodiment, the weight ranges p21 are:
between 0 kg and 10 kg for a baby, and
between 11 kg and 39 kg for a child, and
between 40 kg and 100 kg for an adult.

In one nonlimiting embodiment, the height ranges p22 are:
between 0.8 m and 1 m for a baby, and
between 1.05 m and 1.40 m for a child, and
between 1.45 m and 2 m for an adult.

In a first nonlimiting embodiment, the electronic control unit 13 comprises a classifier 130 (illustrated in FIG. 9) in order to determine volumetric occupancy features P of the passenger compartment 30. The latter are determined according to the persons O present in the passenger compartment 30. The function f5(13, CIR, B, P) described above thus calls for a classifier 130. In one nonlimiting example, the classifier 130 carries out a volumetric occupancy analysis periodically, every 5 seconds in one nonlimiting example.

In one nonlimiting embodiment, the classifier 130 is a support vector machine. The use of a support vector machine is suitable for a motor vehicle application because it does not require too high a consumption in terms of number of computation cycles for the electronic control unit 13 integrated in a motor vehicle 3. It will be noted that a ground truth database Bdd comprising CIR responses each having an associated label SI is used for the learning of the support vector machine, also called the SVM machine. In one nonlimiting embodiment, 1000 CIR responses per label may be used for the learning of the SVM machine.

Thus, in one nonlimiting example, the labels SI are:
1) an unoccupied passenger compartment,
2) an occupancy of the front-right space,
3) an occupancy of the front-left space,
4) an occupancy of the rear-right space,
5) an occupancy of the rear-left space,
6) a baby,
7) a child,
8) an adult,
9) any simple or multiple combination of 2 to 8. This allows cases in which there are several persons O in the passenger compartment 30 to be taken into account.

In another nonlimiting example, instead of the baby, child and adult labels SI, it is possible to have labels SI corresponding to the weight ranges p21 and/or height ranges p22 seen above. Thus, the following labels SI are obtained:
1) an unoccupied passenger compartment, or
2) an occupancy of the front-right space and weight ranges of an adult, and/or
3) an occupancy of the front-left space and weight ranges of an adult, and/or
4) an occupancy of the rear-right space and weight ranges of an adult, and/or
5) an occupancy of the rear-left space and weight ranges of an adult, and/or
6) an occupancy of the front-right space and weight ranges of a child, and/or
7) an occupancy of the front-left space and weight ranges of a child, and/or
8) an occupancy of the rear-right space and weight ranges of a child, and/or
9) an occupancy of the rear-left space and weight ranges of a child, and/or
10) an occupancy of the front-right space and weight ranges of a baby, and/or
11) an occupancy of the front-left space and weight ranges of a baby, and/or
12) an occupancy of the rear-right space and weight ranges of a baby, and/or
13) an occupancy of the rear-left space and weight ranges of a baby, and/or
14) any simple or multiple combination of cases 2 to 13. This allows cases in which there are several persons O in the passenger compartment 30 to be taken into account.

In a first nonlimiting variant embodiment, the classifier 130 receives at the input an impulse response CIR and a time index x for the time at which the impulse response CIR was computed. The classifier 130 generates at the output the volumetric occupancy features P among those mentioned above.

In a second nonlimiting variant embodiment, the classifier 130 receives at the input portions d of the impulse response CIR. To select these portions d, the transceiver 12 that is in reception mode Rx is moreover configured to perform thresholding (function f10(12, CIR, d) illustrated in FIG. 1 or 3). The thresholding is carried out in order to retrieve a portion d1 (illustrated in FIGS. 5 to 8) around a first peak m1 (illustrated in FIGS. 5 to 8) encountered in the impulse response CIR.

Indeed, as illustrated in the nonlimiting examples in FIGS. 5 to 8, the portion d0 does not correspond to any signal, namely it is noise. This portion d0 will be removed by the thresholding. The portion d0 is not representative of the presence of a person O in the passenger compartment 30. The selected portion d2 is representative of the objects situated around the motor vehicle 3, namely outside the motor vehicle 3. It corresponds for example to a distance of 6 meters more compared to the direct propagation path between the transceiver 10 and the transceiver 12. Therefore, it is not necessary for the classifier 130 to take this portion d2 into consideration in order to determine the presence/absence of persons O in the passenger compartment 30. Therefore, this portion d2 will also be removed by the fixed size of d1. In FIGS. 5 to 8, it is possible to see a first peak m1, which is the transmitted signal S1 that arrives directly at the transceiver 12 without encountering an obstacle (namely that takes a direct propagation path), and the other peaks which are reflections of the signal S1 from at least one obstacle such as a person O who is in the passenger compartment 30. Only the portion d1, which corresponds to a distance of up to 3 to 6 meters of detour between the transceiver 10 and the transceiver 12, is taken into account. In one nonlimiting embodiment, the portion d1 that is selected has a duration of between 20 ns (nanoseconds) and 60 ns. This range of values is determined according to the computation power of the electronic control unit 13. It will be noted that 20 ns correspond to approximately 6 meters. This corresponds to a few samples of the impulse response CIR (about twenty or so in one nonlimiting example) around a first peak m1. This allows the reflected signals stemming from the transmitted signal S1 that have bounced back from obstacles inside the passenger compartment 30 and that have therefore taken a path of approximately 6 meters to be taken into account. In the example in FIGS. 5 to 8, the portion d1 is in an interval of time of between 700 ns and 800 ns.

In one nonlimiting embodiment, the electronic control unit 13 is moreover configured to filter the impulse response CIR or the portions d of the impulse response CIR (function f11 (13, CIR(d)) illustrated in FIG. 1 or 3). This allows a purer impulse response CIR to be obtained. In one nonlimiting example, the filtering is performed by means of blind deconvolution.

It will be noted that a single impulse response CIR may be used by the classifier 130 to deduce the volumetric occupancy features P of the passenger compartment 30. In this case, in one nonlimiting embodiment, the transceiver 10 that is in transmission mode Tx is configured to transmit a signal S1 every second. This is enough for the classifier 13 to obtain a classification, namely to obtain the volumetric occupancy features P of the passenger compartment 30.

In a first nonlimiting example, when the volumetric occupancy features P are a combination of the distribution in space p21 and the age category p2, the classifier 130 is used to obtain volumetric occupancy features P classified according to the labels SI cited above in the first nonlimiting example, and used for learning.

In a second nonlimiting example, when the volumetric occupancy features P are a combination of the distribution in space p21 and weight ranges p22 of a person O, the classifier 130 is used to obtain volumetric occupancy features P classified according to the labels SI cited above in the second nonlimiting example, and used for learning.

It will be noted that the classification by the classifier 130 is based on an aggregation of volumetric occupancy features P (if there are combinations). Thus, for example if the following two volumetric occupancy features P are obtained: an occupancy of the front-right space of the vehicle by a child and occupancy of the front-left space by an adult; the classification obtained will provide a single label corresponding to this volumetric occupancy situation.

FIG. 4 illustrates an impulse response CIR when there is nobody in the passenger compartment 30. This is a control impulse response CIR when the motor vehicle 3 is empty. FIG. 5 shows a nonlimiting example illustrating an impulse response CIR of a child who is at the front-left of the passenger compartment 30. FIG. 6 illustrates an impulse response CIR of a child who is at the front-right of the passenger compartment 30. FIG. 7 shows a nonlimiting example illustrating an impulse response CIR of an adult who is at the front-left of the passenger compartment 30. Finally, FIG. 8 shows a nonlimiting example illustrating an impulse response CIR of a child who is at the front-right of the passenger compartment 30 and of an adult who is at the front-left of the passenger compartment 30.

In a second nonlimiting embodiment, the electronic control unit 13 performs a modal decomposition DM (illustrated in FIG. 10). The modal decomposition DM is based on the same principle as the SVM machine, namely the classification of volumetric occupancy features P of the passenger compartment 30, but will take into consideration a sum of volumetric occupancy features P instead of an aggregation. Thus, for example if the following two volumetric occupancy features P are obtained: an occupancy of the front-right space of the vehicle by a child and occupancy of the front-left space by an adult; the classification obtained will provide a set of labels corresponding to sub-volumes of this volumetric occupancy situation. It will be noted that in the same way as for the first embodiment with the classifier 130, in one nonlimiting embodiment, the impulse response CIR is filtered (function f11(13, CIR(d)) illustrated in FIG. 1 or 3).

In a third nonlimiting embodiment, the electronic control unit 13 is configured to perform a spectral analysis SA (illustrated in FIG. 11) on the basis of said impulse response CIR received at the input in order to determine the biometric features B of at least one person O. The function f5(13, CIR, B, P) described above thus calls for a spectral analysis SA. In one nonlimiting embodiment, the biometric features B are a respiratory rate RR and/or a heart rate HR. As illustrated in FIG. 11, in this case, the electronic control unit 13 receives at the input the impulse response CIR and a time index n for the time at which the impulse response CIR was computed. In order to retrieve respiratory cycles and/or heartbeat cycles, in one nonlimiting embodiment, the transceiver 10 that is in transmission mode Tx is configured to transmit a signal S1 at a frequency of between 10 ms (milliseconds) and 50 ms. This allows the transceiver 12 to receive multiple signals S2 corresponding to the signals S1 over the course of time. It will be noted that since the electronic control unit 13 is able to detect the presence/absence A1 of at least one person O and/or the state of health A2 of at least one person O, this third embodiment may be combined with the first embodiment (classifier 130) or the second embodiment (modal decomposition DM).

In one nonlimiting embodiment, for the spectral analysis of a heart rate HR, the electronic control unit 13 retrieves at least 500 impulse responses CIR per minute, or approximately 8.5 impulse responses CIR per second. It will be noted that the average heart rate HR of a person at rest is 70 beats/minute, and between 140 and 250 beats/minute when under stress, concentrating intensely or exerting physical effort. Retrieving 500 impulse responses CIR per minute allows a heart rate to be determined that reaches 250 beats/minute.

In one nonlimiting embodiment, for the spectral analysis of a respiratory rate RR, the electronic control unit 13 retrieves at least 100 impulse responses CIR per minute, or approximately 1.5 impulse responses CIR per second. It will be noted that the average respiratory rate RR of a baby of 6 months is between 25 and 40 breaths/minute, of a child of 3 years is between 20 and 30 breaths/minute, of a child of 6 years is between 18 and 25 breaths/minute and of an adult is between 12 and 18 breaths/minute. Retrieving 100 impulse responses CIR per minute is sufficient to cover the breaths of a baby, a child and an adult.

It will be noted that in the same way as for the first embodiment with the classifier 130, in one nonlimiting embodiment, the impulse response CIR is filtered (function f11(13, CIR) illustrated in FIG. 1 or 2).

In nonlimiting embodiments, the spectral analysis is performed by Fourier transform, by wavelets, by a frequency estimation algorithm called MUSIC (Multiple Signal Classification) known to those skilled in the art, etc.

Thus, the nonlimiting example of spectral analysis by Fourier transform is performed in the following manner. An impulse response CIR is in the time domain. These peaks in time will be analyzed. In one nonlimiting example, portions d1 of the impulse response CIR over time are taken. For example, the portions d1 are taken for 10 impulse responses CIR received over time. Thus, 10 samples of portions d1 are obtained. The Fourier transform is applied to these 10 samples in order to retrieve the peaks in the frequency domain. On the basis of these peaks, the frequency of these peaks is determined and said frequency is compared with reference frequencies expected for a baby, a child, an adult, the reference frequencies being heart rates HR or respiratory rates RR. It will be noted that the heart rates HR and the respiratory rates RR differ in terms of their peak distribution; it is therefore possible to distinguish between them.

As stated above, it is possible to determine the state of health A2 of a person O on the basis of the biometric features B. It will be noted that if there are no changes in the impulse responses CIR over time, this means that there are no movements, for example movements related to breathing or movements related to the heart, in the vehicle and therefore no biometric features B to be collected.

In a first nonlimiting embodiment illustrated in FIG. 1, the analysis device 1 comprises a transceiver 11 that is in transmission mode Tx, and a single transceiver 12 that is in reception mode Rx.

In a second nonlimiting embodiment illustrated in FIG. 3, the analysis device 1 comprises a transceiver 11 that is in transmission mode Tx, and a plurality of transceivers 12 that are in reception mode Rx. In the nonlimiting exemplary implementation illustrated in FIG. 3, the analysis device 1 comprises a transceiver 11 that is in transmission mode Tx, and three transceivers 12 that are in reception mode Rx. Three impulse responses CIR1, CIR2, CIR3 computed by each of the three transceivers 12 are obtained. This allows the transceiver 12 to have a dimension in space. Thus, several points of view are available concerning the presence of at least one person O in the passenger compartment 30. The detection of at least one person O in the passenger compartment 30 of the vehicle 3 will be more precise and more discriminatory. This makes it easier to distinguish between the different situations that could be seen as identical from the point of view of a single transceiver 12. Moreover, this makes it easier to distinguish between multiple persons O in the passenger compartment 30, which is more difficult when a single transceiver 12 in reception mode Rx is used, even if the latter is able to compute multiple impulse responses CIR from a periodically transmitted signal S1.

In this embodiment of a plurality of transceivers 12 that are in reception mode Rx, in the case of the embodiment that calls for a classifier 130, the latter is configured to receive portions d1 of the impulse responses CIR originating from each transceiver 12 (which are in reception mode Rx). In practice, these portions d1 and associated time indices x will be concatenated as an input vector. The position of this information in the input vector reveals the impulse response CIR to which said information belongs. It is thus possible to distinguish between the information of the impulse responses CIR originating from the various transceivers 12. The same goes for the embodiment that calls for the modal decomposition DM.

In this embodiment of a plurality of transceivers 12 that are in reception mode Rx, in the case of the embodiment that calls for a spectral analysis SA, having impulse responses CIR originating from different transceivers 12 makes it possible to determine multiple breaths or multiple heartbeats at once if there are multiple persons O in the passenger compartment 30. This allows a distinction to be drawn between the occupants of the motor vehicle 3 in this way.

When the biometric features B and/or the volumetric occupancy features P have been determined as described above, the electronic control unit 13 is moreover configured to transmit the biometric features B and/or the volumetric features P (function f8(13, 31(F), B, P) illustrated in FIG. 1 or FIG. 3) to an information processing unit 31 that will be able to perform functions F such as safety functions, abnormal state detection functions, energy economy functions, or infotainment functions, etc. These functions F are thus determined according to the biometric features B and/or the volumetric occupancy features P that have been found. In nonlimiting embodiments, the information processing unit 31 is part of the motor vehicle 3 or is not part of the motor vehicle 3. In this latter case, in one nonlimiting example, it is a mobile phone or an identifier of the motor vehicle 3.

In nonlimiting examples, if:

the presence A1 of a child or a baby in the motor vehicle 3 is detected, then the latter is locked, and the function F will be sending a warning message to the mobile phone of the user of the motor vehicle 3 in one nonlimiting example, an abnormal state of health A2 such as, in nonlimiting examples, an abnormal heart rate HR, an abnormal respiratory rate RR, etc., is detected, the function F will be a safety function, such as the transmission of a voice message, an instruction to the driving assistance module of the vehicle to brake, park or automatically stop the vehicle, automated contacting of the relevant authorities, in nonlimiting examples, the presence A1 of multiple persons O in the passenger compartment 30 is detected, the function F will be activation of the heating of the seats in which the various persons O are sitting, supply of power to the screens arranged opposite said persons O, prevention of the rear doors or windows from being opened if there are children or babies, activation of the passenger screen according to one configuration and activation of the driver screen according to another configuration, deactivation of the screens if there is no one in the seats and any other appropriate service depending on the occupancy of the vehicle.

It will be noted that activating/deactivating certain electronic elements of the motor vehicle 3 allows the battery and therefore energy to be saved in particular in the context of electric vehicles.

Thus, the analysis device 1 allows implementation of an analysis method for analyzing a passenger compartment 30 of a vehicle 3. The analysis method 5 is illustrated in FIG. 12. In the illustrated nonlimiting embodiment, the analysis method 5 moreover comprises a step of detecting the presence/absence A1 of persons in the passenger compartment 30, a step of detecting the state of health A2 of at least one person O, and a step of transmitting volumetric features P and/or biometric features B to the information processing unit 31. In one nonlimiting embodiment, the analysis method 5 comprises the following steps.

In a step E1), illustrated F1(10, S1, 11), at least one ultra-wideband transceiver 10 transmits a signal S1 on a wireless communication channel 11. In a step E2), illustrated F2(12, S2, 11), at least one ultra-wideband transceiver 12 receives a signal S2 corresponding to the transmitted signal S1. In a step E3), illustrated F3(12, S1, CIR), said at least one ultra-wideband transceiver 12 computes at least one impulse response CIR of the wireless communication channel 11 from said received signal S2. The impulse response CIR is transmitted to the control unit 13 (step E4, illustrated F4(12, 13, CIR)) and received by the control unit 13 (step E4', illustrated F4'(13, 12, CIR)). In a step E5), illustrated F5(13, CIR, B, P), said electronic control unit 13 determines biometric features B and/or volumetric occupancy features P of the passenger compartment 30 on the basis of said at least one impulse response CIR of the wireless communication channel 11. In one nonlimiting embodiment, the analysis method 5 moreover comprises a step E6), illustrated F6(13, P, O, A1), according to which said electronic control unit 13 determines the presence/absence A1 of persons O in the passenger compartment 30 on the basis of the volumetric occupancy features P of the passenger compartment 30.

In one nonlimiting embodiment, the analysis method 5 moreover comprises a step E7), illustrated F7(13, B, A2), according to which the electronic control unit 13 determines a state of health A2 of at least one person O on the basis of said biometric features B.

In one nonlimiting embodiment, the analysis method 5 moreover comprises a step E8), illustrated F8(13, 31(F), B, P), according to which the electronic control unit 13 transmits volumetric features P and/or biometric features B to an information processing unit 31 in order for the latter to perform a function F determined according to the biometric features B and/or said volumetric occupancy features P that have been found by the analysis of the impulse response CIR or the impulse responses CIR.

It will be noted that steps E6 and E7 may be performed in parallel. It will be noted that since steps E6 to E8 are optional, they are illustrated in broken lines in FIG. 12.

Of course the description of the invention is not limited to the embodiments described above and to the field described above. Thus, the invention also relates to the occupancy of the passenger compartment 30 by at least one animal such as a dog.

It will be noted that it is possible to apply the same principle of analyzing an impulse response CIR originating from an ultra-wideband transceiver 12 in order to detect obstacles outside the motor vehicle 3. Indeed, a signal S1 transmitted by an ultra-wideband transceiver 10 will be reflected from an obstacle that is encountered, and the reflected signal will be received by the ultra-wideband transceiver 12 that is in reception mode Rx. An impulse response CIR will thus be able to be computed and analyzed.

Thus, the described invention especially has the following advantages:

it allows an economic advantage to be attained as it uses UWB transceivers (referenced 10, 12 in the figures), which are already commonly used in motor vehicles, for functions (presence/absence detection, state of health A2 detection and functions F ensuing therefrom) that are different from the PEPS functions for which they are normally used, it allows replacement of dedicated systems for detecting the presence/absence of at least one person O in the passenger compartment 30, and/or his state of health, dedicated systems such as cameras and optical sensors, 89-GHz sensors, etc., it allows automatic detection of persons in the passenger compartment 30 to be carried out without human intervention.

The invention claimed is:

1. An analysis device for analyzing a passenger compartment of a vehicle in order to detect persons said analysis device comprising:

at least one ultra-wideband transceiver configured to transmit a signal on a wireless communication channel; and at least one ultra-wideband transceiver configured to receive a signal corresponding to the transmitted signal, to compute at least one impulse response of the wireless communication channel from said received signal, and to transmit said at least one impulse response of the wireless communication channel to an electronic control unit, wherein said electronic control unit is configured to determine biometric features and volumetric occupancy features of the passenger compartment on the basis of said at least one impulse response of the wireless communication channel, wherein said electronic control unit is configured to perform a modal decomposition based on a classification of the volumetric occupancy features of the passenger compartment by taking into account a sum of the volumetric occupancy features corresponding to different sub-volumes of the passenger compartment, and wherein said electronic control unit filters the impulse response using blind deconvolution prior to determining the biometric features and the volumetric occupancy features.

2. The analysis device as claimed in claim 1, according to which the electronic control unit transmits the biometric features and/or said volumetric occupancy features to an information processing unit in order for the latter to perform a function determined according to the biometric features and/or said volumetric occupancy features.

3. The analysis device as claimed in claim 1, according to which said analysis device comprises an ultra-wideband transceiver configured to transmit a signal and at least two transceivers configured to receive said signal corresponding to said transmitted signal.

4. The analysis device as claimed in claim 1, according to which an ultra-wideband transceiver is configured to be in transmission mode or in reception mode.

5. The analysis device as claimed in claim 1, according to which said electronic control unit is moreover configured to determine the presence of at least one person or the absence of persons in the passenger compartment on the basis of said volumetric occupancy features of the passenger compartment.

6. The analysis device as claimed in claim 1, according to which the volumetric occupancy features of the passenger compartment are a distribution in space, and/or an age category.

7. The analysis device as claimed in claim 6, according to which a distribution in space comprises one or more of:
an unoccupied passenger compartment,
an occupancy of the front-right space,
an occupancy of the front-left space,
an occupancy of the rear-right space, and
an occupancy of the rear-left space.

8. The analysis device as claimed in claim 6, according to which an age category comprises one or more of:
a baby,
a child, and
an adult.

9. The analysis device as claimed in claim 1, according to which said electronic control unit comprises a classifier.

10. The analysis device as claimed in claim 9, according to which said classifier is configured to receive at the input a portion of said at least one impulse response of the communication channel, and a time index for the time at which said impulse response of the communication channel was computed.

11. The analysis device as claimed in claim 9, according to which said classifier is a support vector machine.

12. The analysis device as claimed in claim 1, according to which the biometric features are a respiratory rate and/or a heart rate.

13. The analysis device as claimed in claim 1, according to which said electronic control unit is moreover configured to determine a state of health of at least one person in the passenger compartment of said vehicle on the basis of said biometric features.

14. The analysis device as claimed in claim 1, according to which said electronic control unit is configured to determine said biometric features by a spectral analysis.

15. An analysis method for analyzing a passenger compartment of a vehicle to detect persons, said analysis method comprising:
transmitting, by at least one first ultra-wideband transceiver, a signal on a wireless communication channel;
receiving, by at least one second ultra-wideband transceiver a signal corresponding to the transmitted signal;
computing, by said at least one second ultra-wideband transceiver at least one impulse response of the wireless communication channel from said received signal;
transmitting by said at least one second ultra-wideband transceiver said at least one impulse response of the wireless communication channel to an electronic control unit;
determining by said electronic control unit biometric features and volumetric occupancy features of the passenger compartment on the basis of said at least one impulse response of the wireless communication channel,
wherein said electronic control unit is configured to perform a modal decomposition based on a classification of the volumetric occupancy features of the passenger compartment by taking into account a sum of the volumetric occupancy features corresponding to different sub-volumes of the passenger compartment, and
wherein said electronic control unit filters the impulse response using blind deconvolution prior to determining the biometric features and the volumetric occupancy features.

* * * * *